US009820511B2

(12) United States Patent
Shen et al.

(10) Patent No.: US 9,820,511 B2
(45) Date of Patent: Nov. 21, 2017

(54) HERBAL VAPORIZATION APPARATUS AND METHOD

(71) Applicant: Vape-X Inc., South San Francisco, CA (US)

(72) Inventors: Seibo Ping-Chen Shen, South San Francisco, CA (US); Jeffery Crook, San Francisco, CA (US)

(*) Notice: Subject to any disclaimer, the term of this patent is extended or adjusted under 35 U.S.C. 154(b) by 179 days.

(21) Appl. No.: 14/875,652

(22) Filed: Oct. 5, 2015

(65) Prior Publication Data

US 2016/0021935 A1 Jan. 28, 2016

Related U.S. Application Data

(63) Continuation of application No. 13/367,244, filed on Feb. 6, 2012, now Pat. No. 9,149,586.

(60) Provisional application No. 61/439,963, filed on Feb. 7, 2011.

(51) Int. Cl.
*A24F 47/00* (2006.01)
*A61M 11/04* (2006.01)
*A61M 11/00* (2006.01)
*A61M 16/10* (2006.01)
*A61M 15/08* (2006.01)

(52) U.S. Cl.
CPC ......... *A24F 47/008* (2013.01); *A61M 11/003* (2014.02); *A61M 11/041* (2013.01); *A61M 11/042* (2014.02); *A61M 16/107* (2014.02); *A61M 15/08* (2013.01); *A61M 2205/3368* (2013.01); *A61M 2205/3606* (2013.01); *A61M 2205/3653* (2013.01); *A61M 2205/505* (2013.01); *A61M 2205/8206* (2013.01)

(58) Field of Classification Search
CPC ...... A24F 47/00; A24F 47/002; A24F 47/004; A24F 47/008; A61M 11/0041; A61M 15/00
USPC ........ 219/243, 260–270; 131/360, 194, 273; 128/200.14
See application file for complete search history.

(56) References Cited

U.S. PATENT DOCUMENTS

| | | | | |
|---|---|---|---|---|
| 4,284,089 A | * | 8/1981 | Ray | A24F 47/002 128/202.21 |
| 5,080,114 A | * | 1/1992 | Rudolph | A24F 47/004 131/194 |
| 5,665,262 A | * | 9/1997 | Hajaligol | A24F 47/008 131/194 |
| 6,095,153 A | * | 8/2000 | Kessler | A24F 47/008 131/194 |
| 7,415,892 B2 | * | 8/2008 | Lam | G01F 1/58 73/861.15 |

(Continued)

*Primary Examiner* — Michael Laflame, Jr.
(74) *Attorney, Agent, or Firm* — Myers Berstein LLP

(57) ABSTRACT

The subject technology pertains to an herbal vaporization apparatus including an electric heat base comprising a glass pass-through tube, and a hydratube having a first end a second end, wherein the hydratube is configured to be removably coupled with the electric heat base at the second end to place the hydratube in fluidic communication with the glass pass-through tube. The electric heat base can be configured to be coupled to the hydratube such that the hydratube is vertically mounted on top of the electric heat base. The electric heat base can include a glass pass-through tube including a plurality of chambers separated by constrictions and configured to receive and transmit a volume of gas, and a heating element disposed adjacent to the glass pass-through tube to heat the volume of gas received by the glass pass-through tube. Furthermore, the herbal vaporization apparatus can also include an herbal containment unit.

18 Claims, 6 Drawing Sheets

(56) References Cited

U.S. PATENT DOCUMENTS

| | | | | |
|---|---|---|---|---|
| 7,458,374 B2* | 12/2008 | Hale | .................. | A24F 47/006 |
| | | | | 128/203.26 |
| 8,365,742 B2* | 2/2013 | Hon | .................. | A24F 47/008 |
| | | | | 128/202.21 |
| 8,495,998 B2* | 7/2013 | Schennum | ............ | A24F 47/002 |
| | | | | 128/200.17 |
| 9,027,565 B2* | 5/2015 | Wagenhals | ............... | A24F 13/04 |
| | | | | 128/200.11 |
| 2002/0079309 A1* | 6/2002 | Cox | .................. | A61M 11/041 |
| | | | | 219/486 |
| 2005/0235991 A1* | 10/2005 | Nichols | ................ | A61M 15/00 |
| | | | | 128/204.17 |
| 2007/0267031 A1* | 11/2007 | Hon | .................. | A24F 47/008 |
| | | | | 131/273 |
| 2008/0023003 A1* | 1/2008 | Rosenthal | ............ | A61M 11/041 |
| | | | | 128/203.26 |
| 2008/0230052 A1* | 9/2008 | Montaser | .......... | A61M 15/0085 |
| | | | | 128/200.16 |
| 2010/0181387 A1* | 7/2010 | Zaffaroni | ............... | A61M 15/06 |
| | | | | 239/13 |
| 2010/0236546 A1* | 9/2010 | Yamada | ............... | A61M 11/042 |
| | | | | 128/200.21 |
| 2010/0242956 A1* | 9/2010 | Yamada | ............... | A61M 11/041 |
| | | | | 128/200.23 |
| 2010/0242974 A1* | 9/2010 | Pan | .................. | A24F 47/008 |
| | | | | 131/273 |
| 2011/0011396 A1* | 1/2011 | Fang | .................. | A24F 47/008 |
| | | | | 128/202.21 |
| 2011/0232654 A1* | 9/2011 | Mass | .................. | A61M 15/06 |
| | | | | 131/273 |

* cited by examiner

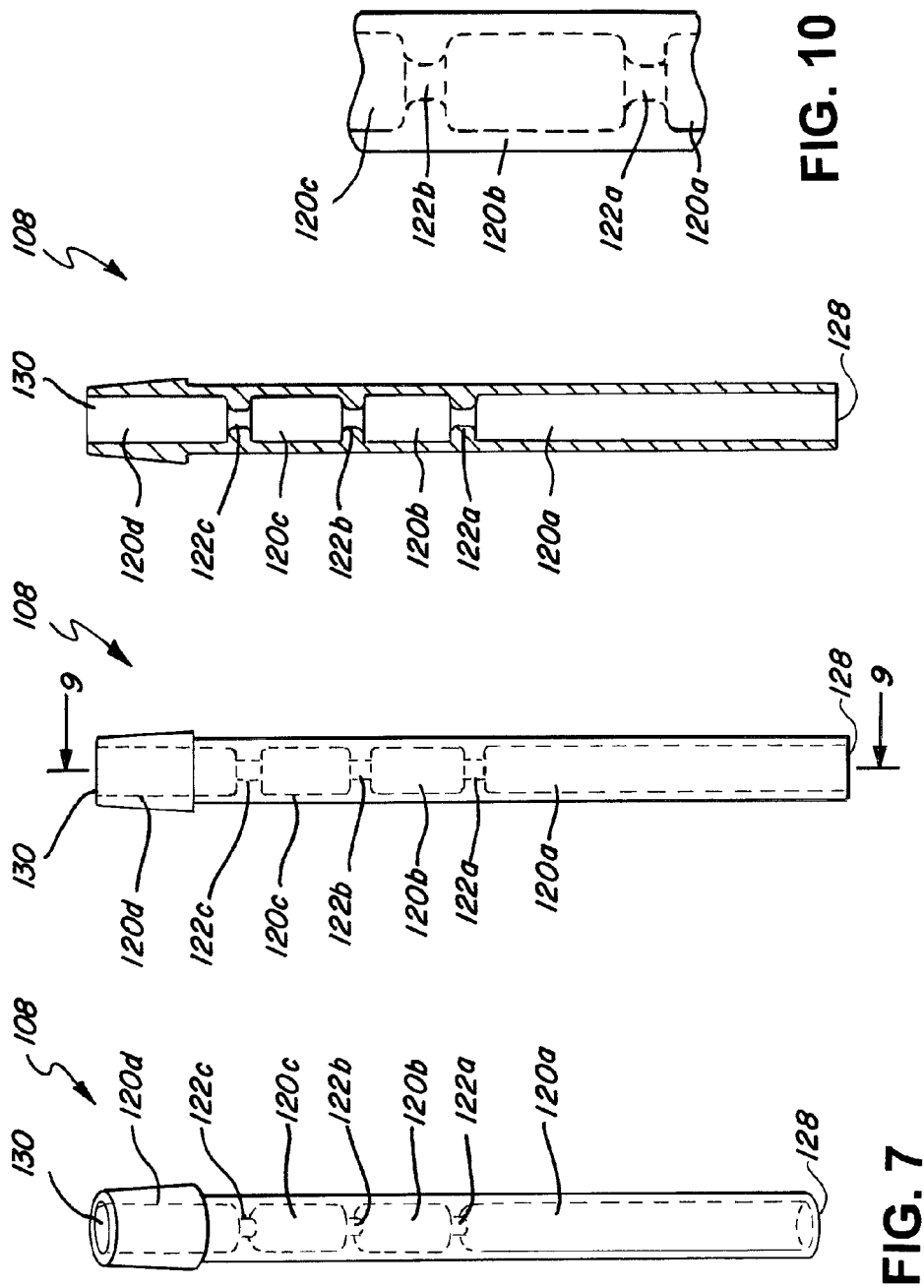

HERBAL VAPORIZATION APPARATUS AND METHOD

The present application is a continuation of U.S. application Ser. No. 13/367,244, filed on Feb. 6, 2012, which claims priority to U.S. Provisional Application No. 61/439,963 filed on Feb. 7, 2011, entitled "VAPORIZER SYSTEMS AND METHODS," both of which are fully incorporated by reference herein.

FIELD

The subject disclosure relates generally to an herbal vaporization apparatus and method for use in producing herbal vapor for inhalation by a user. More specifically, the subject disclosure pertains to an herbal vaporization apparatus which comprises a hydratube for cooling and conditioning the herbal vapor.

BACKGROUND

In conventional vaporizer products, herbal vapor is passed over ceramic or metal surfaces (for heating) and contacts adhesives and plastics before delivery to a user. This can be problematic, especially for users requiring safe, long-term use, as these types of materials are known to affect taste present potential health hazards.

SUMMARY

The disclosed subject matter relates to an herbal vaporization apparatus including an electric heat base comprising a glass pass-through tube, and a hydratube having a first end, a second end, wherein the hydratube is configured to be removably coupled with the electric heat base at the second end to place the hydratube in fluidic communication with the glass pass-through tube. In other aspects the disclosed subject matter includes an herbal containment unit configured to contain an herbal composition, and be located between the electric heat base and the hydratube.

In yet another implementation, the disclosed subject matter relates to an herbal vaporization apparatus including a hydratube, an electric heat base configured to be coupled to the hydratube such that the hydratube is vertically mounted on top of the electric heat base. In certain aspects of the disclosed subject matter, the electric heat base includes a glass pass-through tube including a plurality of chambers separated by constrictions and configured to receive and transmit a volume of gas, and a heating element disposed adjacent to the glass pass-through tube to heat the volume of gas received by the glass pass-through tube. Furthermore, the herbal vaporization apparatus can also include an herbal containment unit configured to contain an herbal composition, and be in fluidic communication with the glass pass-through tube and the hydratube.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative, and not restrictive in nature.

BRIEF DESCRIPTION OF THE DRAWINGS

Certain features of the subject technology are set forth in the appended claims. However, for the purpose of explanation, several embodiments of the subject technology are set forth in the following figures.

FIG. 7 illustrates an example of a perspective view of a glass pass-through tube of an herbal vaporization apparatus, according to some aspects of the subject disclosure.

FIG. 8 illustrates an example of a side view of a glass pass-through tube of an herbal vaporization apparatus, according to some aspects of the subject disclosure.

FIG. 9 illustrates an example of a cross-sectional view of a glass pass-through tube of an herbal vaporization apparatus, according to some aspects of the subject disclosure.

FIG. 10 illustrates an example of a close-up view of a portion of a glass pass-through tube of an herbal vaporization apparatus, according to some aspects of the subject disclosure.

DETAILED DESCRIPTION

The detailed description set forth below is intended as a description of various configurations of the subject technology and is not intended to represent the only configurations in which the subject technology can be practiced. The appended drawings are incorporated herein and constitute a part of the detailed description. The detailed description includes specific details for the purpose of providing a more thorough understanding of the subject technology. However, it will be clear and apparent to those skilled in the art that the subject technology is not limited to the specific details set forth herein and may be practiced without these specific details. In some instances, well-known structures and components are illustrated in a simplified form in order to avoid obscuring the concepts of the subject technology.

Figure 1:
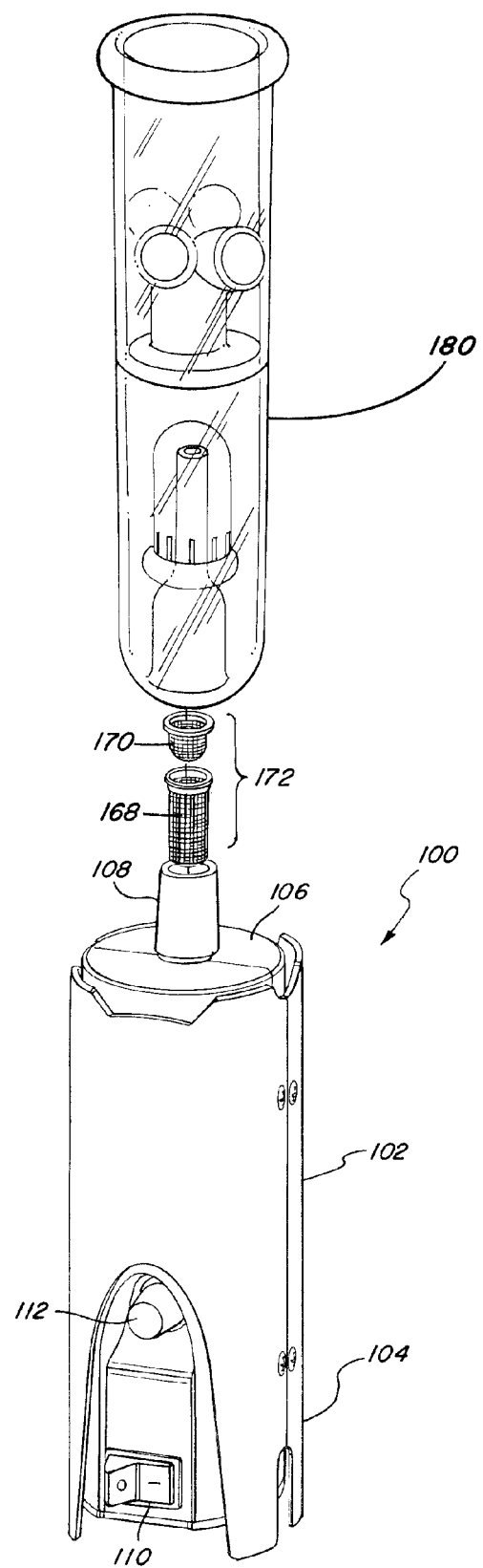
FIG. 1 illustrates an example of an herbal vaporization apparatus, according to some aspects of the subject disclosure.
Figure 2:
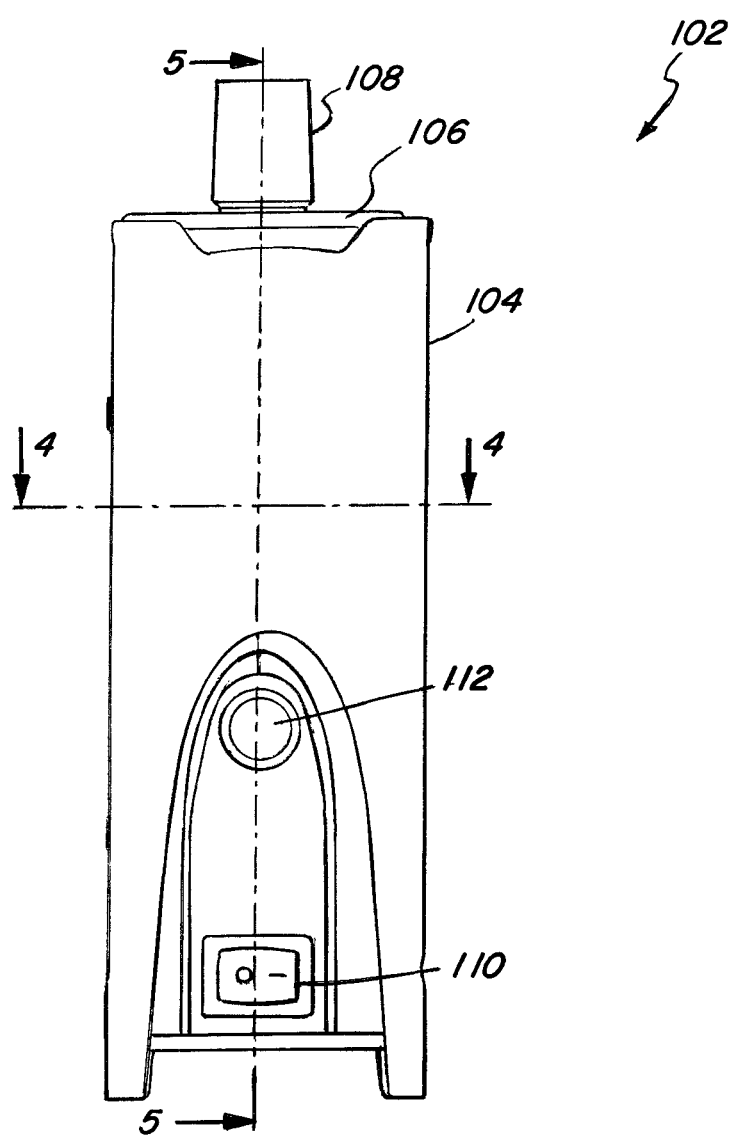
FIG. 2 illustrates an example of a front view of an herbal vaporization apparatus, according to some aspects of the subject disclosure.
Figure 4:
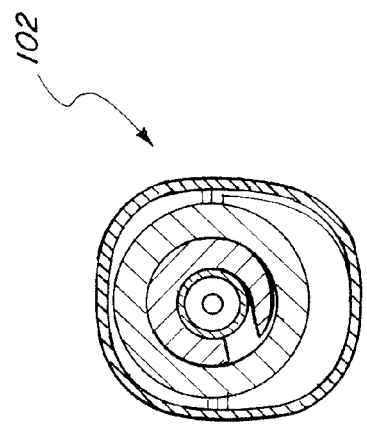
FIG. 4 illustrates an example of a cross-sectional view of an herbal vaporization apparatus, according to some aspects of the subject disclosure.

As seen in FIG. 1, the subject technology relates to an herbal vaporization apparatus 100 (i.e., a vaporizer) for use in generating inhalable herbal vapor for a user. In certain aspects, the herbal vaporization apparatus 100 comprises a hydratube 180 that is fixed on the top side of an electric heat base 102, such that the hydratube is positioned in an upright vertical orientation relative to the electric heat base 102. When a user inhales from the top of the hydratube (i.e., a first end of the hydratube) ambient air is drawn in through an opening in the electric heat base 102 where it is heated while passing through a pass-through tube 108. The heated air is then passed over an herbal composition stored in an herbal containment unit 172 to produce herbal vapor, which flows up the hydratube 180 to be inhaled by the user.

The herbal containment unit 172 can include, for example, herbal containers 168 and 170. The herbal composition can be placed in the herbal container 168, while the herbal container 170 can be placed within the herbal container 168 and on top of the herbal composition to secure the herbal composition. The herbal composition can include any type of organic composition, for example, tobacco, flavored tobacco, volatile herbs, and/or any other type of herbs which can produce desirable herbal vapors when heated.

In an embodiment, the herbal containers 168 and 170 can be formed of a stainless steel mesh or other material with apertures to allow the heated air to pass through the herbal containers in order to heat and vaporize the herbal composition. The apertures should be sized small enough such that the herbal composition does not fall through the apertures, and large enough such that sufficient heated air can pass through to heat the herbal composition and produce the herbal vapor. The herbal containment unit 172 can be placed between the electric heat base 102 and the hydratube 180. In an embodiment, the herbal containment unit 172 can be placed within a portion of the pass-through tube 108.

Figure 3:
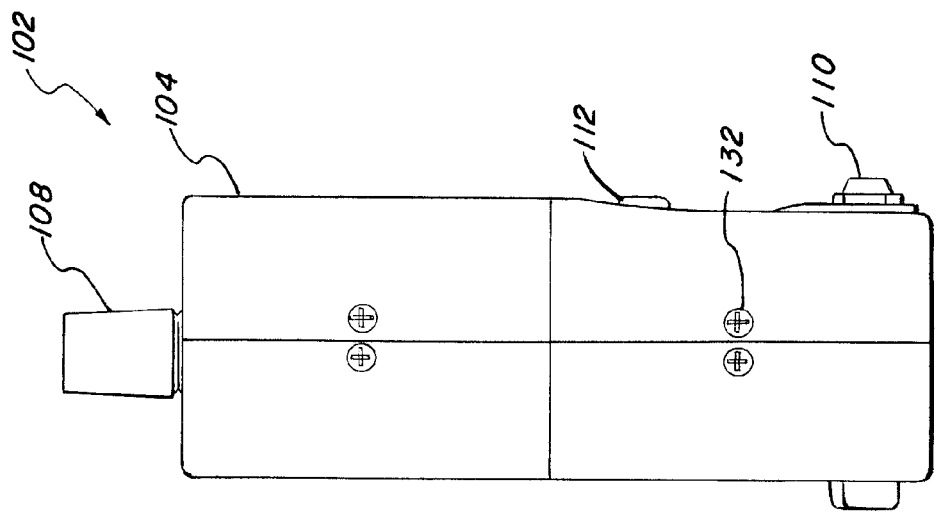
FIG. 3 illustrates an example of a side view of an herbal vaporization apparatus, according to some aspects of the subject disclosure.
Figure 6:
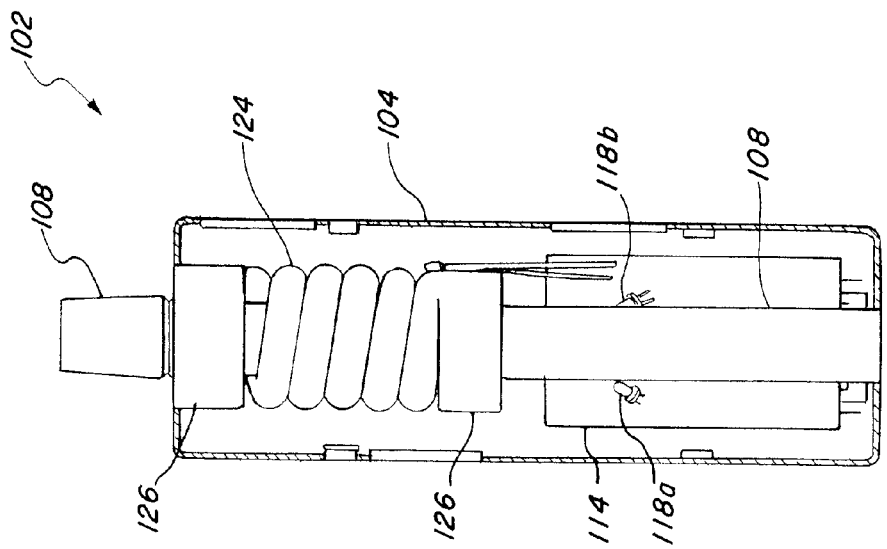
FIG. 6 illustrates an example of an open side view of an herbal vaporization apparatus, according to some aspects of the subject disclosure.

As seen in FIGS. 1-6, the electric heat base 102 includes, for example, an outer enclosure 104, and an inner enclosure 106. In an embodiment, the outer enclosure 104 can be formed, for example, from a metallic substance, such as aluminum. The outer enclosure 104 can be secured to the inner enclosure 106 through fasteners 132 (FIGS. 1 and 3). The fasteners 132 can be, for example, screws, rivets, or any other type of device capable of securing the outer enclosure 104 to the inner enclosure 106. Furthermore, a feed-through grommet 116 (FIG. 5) can be utilized to secure a power cord (not shown). In an embodiment, the outer enclosure 104 and the inner enclosure 106 can be separated, for example, by an insulative element. The insulative element can be constructed of any suitable insulating material. In certain aspects, the insulative element will comprise a vacuum.

The inner enclosure 106 can be formed, for example, from an insulating material. Such an insulating material can be heat-reflective. In some examples, the insulating material may be disposed around a heating element 124 and configured to reflect heat from the heating element 124 (FIGS. 5 and 6) in an inward direction toward the pass-through tube 108, which will be described in more detail later.

The electric heat base 102 also includes a power switch 110 and an activation switch 112. The power switch 110 turns the electric heat base 102 on or off, while the activation switch 112 activates the electric heat base 102 such that the electric heat base generates the heated air which is passed through the herbal composition. When the power switch 110 is turned on, a light emitting diode (LED) 118a (FIGS. 5 and 6) can be illuminated to indicate that the electric heat base 102 is turned on and powered, but has not been activated, yet. When the activation switch 112 is depressed and the electric heat base 102 is activated, the LED 118b (FIG. 6) can be illuminated to indicate that the electric heat base 102 is activated. In an embodiment, the LED 118a can be of a first color, while the LED 118b can be of a second color different than the first color. Furthermore, the LEDs 118a and 118b can provide alternative user feedback such as indication of heating, ready for use, temperature adjustment, overheating of the electric base unit 102, or other type of information which may be helpful to the user. Additional LEDs may also be used to provide additional user feedback.

The heating element 124 (FIGS. 5 and 6) can be wrapped around the pass-through tube 108. When the activation switch 112 is depressed and the electric heat base 102 is activated, the heating element 124 is activated and begins to heat the air in the pass-through tube 108. In an embodiment, the heating element 124 can heat the air in the pass-through tube 108 to hundreds of degrees Fahrenheit. In an embodiment, the heating element 124 can be connected to and powered by a rechargeable battery.

Since the heating element 124 is not located within the pass-through tube 108, the air does not interact with the components of the heating element 124. Therefore, the location of the heating element 124 allows it to not affect the taste of the air in the pass-through tube 108, and subsequently the herbal vapor, as the air is being heated by the heating element 124. The configuration of the heating element 124 relative to the pass-through tube 108 allows the pass-through tube 108 to thermally expand or contract with changes in temperature without risk of cracking or damaging the pass-through tube 108.

To ensure that the heat from the heating element 124 is directed towards the air in the pass-through tube 108, the inner enclosure 106 can reflect the heat from the heating element 124 onto the pass-through tube 108. Furthermore, insulation 126 can also be used to direct heat towards the pass-through tube 108. Both the inner enclosure 104 and the insulation 126 can also reduce an amount of heat transmitted to the outer enclosure 102. In an embodiment, the insulation 126 can be, for example, a microtherm insulation. The insulative element disclosed above, such as the vacuum, can also aid in maintaining the heating element 124 at a substantially constant temperature.

In an embodiment, this can allow a user to grip the electric heat base 102 without burning their hand. Furthermore, the heating element 124 can also be wrapped in insulating material. Although in FIGS. 5 and 6, the heating element 124 is depicted as a flexible wire heater rope, other types of heating devices can be used to heat the air in the pass-through tube 102. However, the heating element 124 should be located outside the pass-through tube 102 to reduce the introduction of any flavoring from the air contacting the heating element 124.

In addition, a temperature sensing unit 134 (FIG. 6) can be placed adjacent the heating element 124 to detect temperature data corresponding to a temperature of the heating element 124. In an embodiment, the temperature sensing unit 134 can be, for example, a thermistor.

Figure 5:
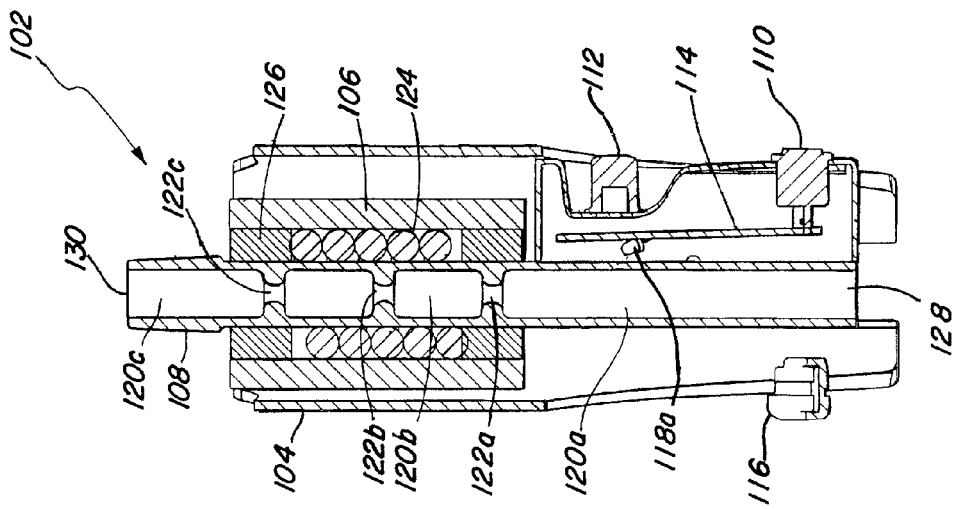
FIG. 5 illustrates an example of a cross-sectional view of an herbal vaporization apparatus, according to some aspects of the subject disclosure.

The electric heat base 102 can also include, for example, a printed circuit board 114 (FIG. 5). The printed circuit board 114 can include a microcontroller coupled to the power switch 110, the activation switch 112, the heating element 124, and/or the temperature sensing unit 134. The heating element 124 can receive the temperature data from the temperature sensing element 134 and control the operation of the heating element 124. For example, if the temperature sensing unit 134 transmits temperature data to the controller indicating that the temperature of the heating element 124 is too high or too low, then the controller can increase or decrease the current flowing through the heating element 124 to maintain the heating element 124 at a substantially constant temperature. Thus the controller can, for example, prevent the heating element 124 from overheating. The controller can also maintain a substantially constant temperature for the heated air flowing through the pass-through tube 108.

In an embodiment, the microcontroller can also be configured to power off the heating element 124 after a predetermined amount of time. This can, for example, reduce a likelihood that the heating element 124 will be accidentally left on for too long. The predetermined amount of time can be a time sufficient to allow for a desirable quantity of herbal vapors to be generated from the heating of the herbal composition, but short enough to prevent or reduce a likelihood of an accident. In an embodiment, the microcontroller can be configured to receive data from and to send data to a wireless processor-based device. The microcontroller can also, for example, be configured to send information to and receive information from a touch-screen display. Such information can include, for example, heating time, temperature data, on/off time, activation time, or any other type of useful information.

As previously noted, when the user inhales through the hydratube 180, a negative pressure is created at a first end of the pass-through tube 108, which allows ambient air to flow into the pass-through tube 108 at a second end of the pass-through tube, such that the air can be heated by the heating element 124 before exiting the pass-through tube 108 at the first end of the pass-through tube 108 and passing into the affixed hydratube 180. Referring to FIGS. 1, 5, and 7-10, the pass-through tube 108 includes, for example, and an outlet 130 located at the first end of the pass-through tube 108, and an inlet 128 located at the second end of the pass-through tube. The ambient air flows through into the pass-through tube 108 through the inlet 128 and exits the pass-through tube 108 through the outlet 130. In an embodiment, the pass-through tube 108 is formed from glass. Advantageously, glass is relatively inert. Thus it does not generally react with the air passing through the pass-through tube 108. This can prevent or reduce, for example, any tainting or flavoring of the air, and subsequently the herbal vapor, caused by the pass-through tube 108.

In an embodiment, the pass-through tube 108 includes multiple chambers, such as chambers 120*a*, 120*b*, 120*c*, and 120*d* which the air passes through from the inlet 128 to the outlet 130. The inlet 128 is located at an end of the chamber 120*a*, while the outlet 130 is located at an end of the chamber 120*d*. Although four chambers are shown, other number of chambers can also be used.

Constrictions 122*a*, 122*b*, and 122*c* separate the chambers 120*a*, 120*b*, 120*c*, and 120*d*. In an embodiment, the constrictions 122*a*, 122*b*, and 122*c* slow the flow of the air from inlet 128 to the outlet 130. If the air flows too fast from the inlet 128 to the outlet 130, the air may not be sufficiently heated by the heating element 124. However, if the air flows too slowly, the air may be heated too much by the heating element 124. Thus, the differential in air speed can reduce the consistency of the air temperature. Thus, the constrictions 122*a*, 122*b*, and 122*c*, can allow the air to flow through the pass-through tube 108 at a more constant speed, allowing for the air to be heated to a substantially consistent temperature and reduce variations in the temperature of the air exiting the outlet 130.

In an embodiment, the constrictions 122*a*, 122*b*, and 122*c*, can also cause swirls in the air passing through the pass-through tube 108. Air that is flowing through the pass-through tube 108 closer to the heating element 124, such as near the outer portion of the pass-through tube 108 will generally be hotter than the air further away from the heating element 124, such as towards the center of the pass-through tube 108. This can cause the air to be unevenly heated across a cross-section of the pass-through tube 108 when the air exits the outlet 130. The unevenly heated air across the cross-section of the pass-through tube 108 can undesirably burn the herbal composition in an uneven manner with some portions of the herbal composition being burnt or even charred, with other portions of the herbal composition being barely burnt.

However, the swirling caused by the constrictions 122*a*, 122*b*, and 122*c* can cause air closer to the heating element 124 to mix with the air further away from the heating element 124. This mixing of the air can homogenize the temperature of the air such that the temperature of the air is substantially consistent across the cross-section of the pass-through tube 108 as it exits the outlet 130. This can lead to a more desirable and consistent heating of the herbal composition. Although three constrictions are shown, other numbers of constrictions may be used which may generate sufficient swirl to evenly heat the air at the cross-section of the pass-through tube 108.

In an embodiment, the pass-through tube 108 can also include, for example, protrusions or grooves located on one or more of the chambers 120*a*, 120*b*, 120*c*, or 120*d*. The protrusions or grooves can also aide in generating swirls in the air passing through the pass-through tube 108. In an embodiment, the pass-through tube 108 could also comprise, for example, other materials such as aluminum, metal, ceramics, or other types of substances that may facilitate transfer of heated air.

Figure 11:
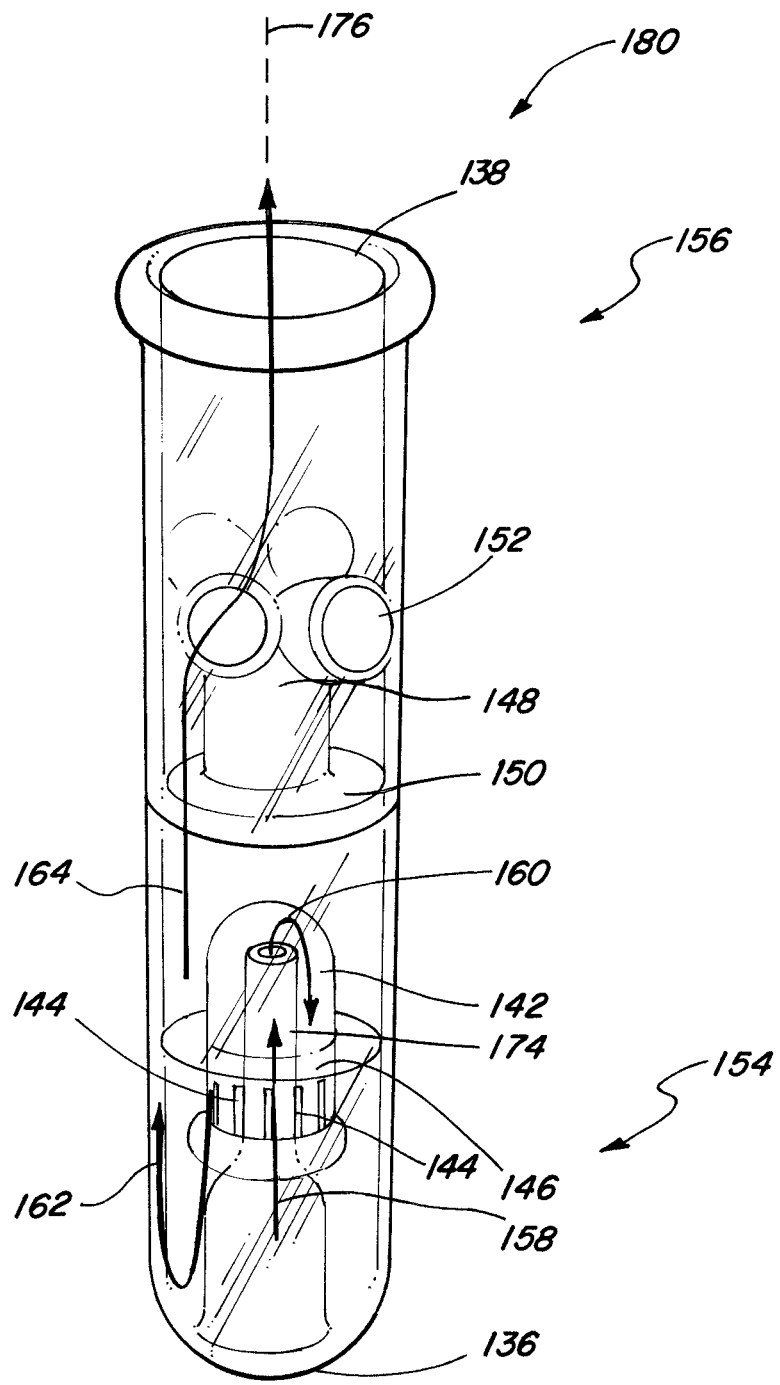
FIG. 11 illustrates an example of a hydratube of an herbal vaporization apparatus, according to some aspects of the subject disclosure.

The hydratube 180 which receives the herbal vapor from the heating of the herbal composition can be seen, for example, in FIG. 11. The hydratube 180 is in fluidic communication with the electric heat base 102 and is configured to be removably connected to the electric heat base 102 at a second end 136. When connected to the electric heat base 102, a user's inhalation of air at a first end 138 of the hydratube 180 causes air to flow through the electric heat base 102, the herbal composition in the herbal containment unit 172, and into the second end 136 of the hydratube 180 as herbal vapor. The hydratube 180 includes a first portion 156 and a second portion 154. The first end 138 is located at the first portion 156, while the second end 136 is located at the second portion 154. Generally, the herbal vapor from the electric heat base 102 and the herbal containment unit 172 flows from the second portion 154 to the first portion 156.

As can be seen, the hydratube 180 can store water 146. Generally the water 146 has a water level above slits 144 of a containment dome 142, but below an exit of a receiving tube 174. When the hydratube 180 receives the herbal vapor from the electric heat base 102 and the herbal containment unit 172, the herbal vapor flows through a receiving tube 174 as indicated by an arrow 158. Upon exit of the receiving tube 174, the herbal vapor is diverted downwards by the containment dome 142 as indicated by an arrow 160. The herbal vapor enters the water 146 and exits through the slits 144 while still immersed in the water 146. The herbal vapor then exits the water 146 and travels towards the first portion 156 as indicated by an arrow 162. The flow of the herbal vapor through the water 146 generally cools the herbal vapor to a desirable temperature so that the user does not burn his lungs with herbal vapor that is too hot. Furthermore, the water can also filter the herbal vapor to remove undesirable material or particulates. In an embodiment, the receiving tube 174 and the containment dome 142 can form, for example, a percolator. Although a single percolator is shown, additional percolators may also be used.

The second portion 154 and the first portion 156 are joined by a ring 150. The ring has a smaller inner diameter than the second portion 154 and the first portion 156. The ring 150 can function as a splash guard to reduce the likelihood that water will be inhaled by the user if the water 146 is bubbling due to the exiting of the herbal vapor through the water 146. The herbal vapor then travels through the exiting tube 148 and can be inhaled by the user. Optionally, the second portion 154 can also include cooling units 152. The cooling units 152 allow for cooling material such as ice to be placed adjacent the exiting tube 148. This allows for further cooling of the herbal vapor. Furthermore, the cooling units 152 can also function as additional splash guards to further reduce the likelihood that the user will inhale water.

In an embodiment, the first end 138 and the second end 136 of the hydratube 180 are both centered on a vertical axis 176 of the hydratube 180. The hydratube 180 can also be vertically symmetrical. This can allow for the hydratube 180 to be easily mated onto the electric heat base 102 in a vertical configuration such that the user can operate the herbal vaporization apparatus 100 with a single hand. This can be especially beneficial, for example, for users with arthritis or other illnesses which may prevent the user from utilizing both hands or make it uncomfortable for the user to use both hands to operate the herbal vaporization apparatus 100.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the systems and methods is not intended to be exhaustive or to limit the systems and methods to the precise forms disclosed. While specific embodiments of, and examples for, the systems and methods are described herein for illustrative purposes, various equivalent modifications are possible within the scope of the systems and methods, as those skilled in the relevant art will recognize. The teachings of the systems and methods provided herein can be applied to other systems and methods, not only for the systems and methods described above.

The elements and acts of the various embodiments described above can be combined to provide further embodiments. These and other changes can be made to the systems and methods in light of the above detailed description.

What is claimed is:

1. A heater for heating an herbal composition, the heater comprising:
   an enclosure;
   a pass-through tube at least partially within the enclosure, the pass-through tube having an inlet, an outlet, an inner wall, an outer wall and an inner diameter, the inlet configured for drawing air into the pass-through tube, the outlet configured to deliver air at an increased temperature to the herbal composition, the inner wall having a first protrusion reducing the inner diameter of the pass-through tube at a first part of the inner wall and a second protrusion reducing the inner diameter of the pass-through tube at a second part of the inner wall downstream from the first part of the inner wall;
   a chamber defined between the first constriction and the second constriction;
   an electric heating element within the enclosure and positioned outside of the pass-through tube and adjacent to at least a portion of the outer wall of the pass-through tube, the electric heating element configured for heating the air flowing within the pass-through tube; and
   an insulating material at least partially surrounding the electric heating element, the first constriction, the second constriction, and the chamber;
   wherein the protrusion causes a disturbance in the air to increase thermal mixing within the air.

2. The heater of claim 1 wherein the first protrusion is a first annular constriction of the inner wall and the second protrusion is a second annular constriction of the inner wall.

3. The heater of claim 2 wherein a the insulating material fully surrounds the electric heating element, the first constriction, the second constriction, and the chamber.

4. The heater of claim 1 wherein the first part of the inner wall is opposite the portion of the outer wall, and the second part of the inner wall is opposite a second portion of the outer wall, the electric heating element being located over at least one of the portion and the second portion of the outer wall.

5. The heater of claim 1 wherein the electric heating element surrounds the pass-through tube.

6. The heater of claim 5 wherein the electric heating element is a flexible heating element wrapped about the portion of the pass-through tube.

7. The heater of claim 1 wherein the enclosure further comprises an inner enclosure within and an outer enclosure, the inner enclosure separated from the outer enclosure.

8. The heater of claim 7 wherein the inner enclosure separated from the outer enclosure by an insulating space.

9. The heater of claim 8 wherein the space between the inner enclosure and the outer enclosure includes an insulating material.

10. The heater of claim 1 wherein the enclosure includes a base portion that is configured to rest on a support surface to orient the pass-through tube substantially vertically so that the outlet is directed upwardly and the inlet is spaced apart from the support surface.

11. The heater of claim 10 wherein a water containment tube comprises a receiving tube directed inwardly into the tube, water capable of being contained between the water containment tube and the receiving tube, the water containment tube being mounted to the heater with the outlet of the pass-through tube inserted into the receiving tube.

12. The heater of claim 11 wherein an herbal containment unit is positioned within the outlet of the pass-through tube.

13. A heater for heating an herbal composition, the heater comprising:
   an insulated enclosure;
   a pass-through tube at least partially within the insulated enclosure, the pass-through tube having an inlet, an outlet, an inner wall, an outer wall and an inner diameter, the inlet configured for drawing air into the pass-through tube, the outlet configured to deliver air at an increased temperature to the herbal composition, the inner wall having a first annular constriction and a second annular constriction, the first annular constriction and the second annular constriction defining a chamber therebetween; and
   an electric heating element within the insulated enclosure and positioned outside of the pass-through tube and adjacent to at least a portion of the outer wall of the pass-through tube, the electric heating element configured for heating the air flowing within the pass-through tube;
an insulating material at least partially surrounding the electric heating element, the first annular constriction, the second annular constriction, and the chamber;
wherein the annular constriction causes a disturbance in the air to increase thermal mixing within the air.

14. The heater of claim 13 wherein the first annular constriction is located at a first part of the inner wall which is opposite the portion of the outer wall.

15. The heater of claim 13 wherein the electric heating element surrounds the pass-through tube about the chamber.

16. The heater of claim 15 wherein the electric heating element is a flexible heating element wrapped about the portion of the pass-through tube.

17. The heater of claim 13 wherein the insulating material completely surrounds the electric heating element, the first annular constriction, the second annular constriction, and the chamber.

18. The heater of claim 13 wherein the insulating material completely surrounds the electric heating element, the first constriction, the second constriction, and the chamber.

* * * * *